US007524940B2

(12) United States Patent
Pelleymounter et al.

(10) Patent No.: US 7,524,940 B2
(45) Date of Patent: Apr. 28, 2009

(54) OB PROTEIN COMPOSITIONS AND METHODS

(75) Inventors: Mary Ann Pelleymounter, Thousand Oaks, CA (US); Randy Ira Hecht, Thousand Oaks, CA (US); Michael Benjamin Mann, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 585 days.

(21) Appl. No.: 10/214,037

(22) Filed: Aug. 5, 2002

(65) Prior Publication Data

US 2003/0054997 A1 Mar. 20, 2003

Related U.S. Application Data

(63) Continuation of application No. 09/366,133, filed on Aug. 2, 1999, now abandoned, which is a continuation of application No. 08/920,608, filed on Aug. 27, 1997, now abandoned, which is a continuation of application No. 08/474,833, filed on Jun. 7, 1995, now abandoned.

(51) Int. Cl.
*C07K 1/14* (2006.01)
*C07K 14/00* (2006.01)

(52) U.S. Cl. .................. 530/412; 530/350; 530/228

(58) Field of Classification Search ........................ None
See application file for complete search history.

(56) References Cited

U.S. PATENT DOCUMENTS

| 4,179,337 | A |   | 12/1979 | Davis et al. ................. 435/181 |
| 5,320,840 | A | * | 6/1994  | Camble et al. ............. 424/85.1 |
| 5,359,034 | A |   | 10/1994 | Skelly et al. ................ 530/351 |
| 5,523,089 | A | * | 6/1996  | Bergstrom et al. ....... 424/262.1 |
| 6,048,837 | A | * | 4/2000  | Friedman et al. ............... 514/2 |
| 6,429,290 | B1| * | 8/2002  | Friedman et al. ........... 530/350 |

FOREIGN PATENT DOCUMENTS

| AU |        6817631 A | * | 12/1988 |
| EP |        0 401 384 |   | 12/1990 |
| WO |      WO 89/10932 |   | 11/1989 |
| WO |      WO 96/05309 |   |  2/1996 |

OTHER PUBLICATIONS

Ngo et al., 1994, The Protein Folding Problem and Tertiary Structure Prediction, pp. 492-495.*

Wells, Aditivity of Mutational Effects in Proteins, 1990, Biochemistry, vol. 26, No. 37, pp. 8509-8517.*
Bachmann et al. (1976), "Recalibrated Linkage Map of *Escherichia coli* K-12", *Bacteriol. Rev.* 40(1):116-167.
Das (1990), "Overproduction of Proteins in *Escherichia coli*: Vectors, Hosts, and Strategies", *Methods in Enzymology* 8: 93-112.
De Vos et al. (1995), "Induction of *ob* Gene Expression by Corticosteroids Is Accompanied by Body Weight Loss and Reduced Food Intake", *J. Bio. Chem.* 270(27):15958-15961.
Francis (1992), "Protein modification and fusion proteins", *Focus on Growth Factors* 3:4-10.
Frederich et al. (1995), "Leptin levels reflect body lipid content in mice: Evidence for diet-induced resistance to leptin action", *Nature Medicine* 1(12):1311-1314.
Halaas et al. (1995), "Weight-Reducing Effects of the Plasma Protein Encoded by the *obese* Gene", *Science* 269:543-546.
Houseknecht et al. (1996), "Evidence for Leptin Binding to Proteins in Serum of Rodents and Humans: Modulation with Obesity", *Diabetes* 45:1638-1643.
Levin et al. (1996), "Decreased food intake does not completely account for adiposity reduction after ob protein infusion", *P.N.A.S. USA* 93:1726-1730.
Malik et al. (1992), "Polyethylene Glycol (PEG)-modified Granulocyte-Macrophase Colony-stimulating Factor (GM-CSF) with Conserved Biological Activity", *Exp. Hematol.* 20:1028-1035.
Pelleymounter et al. (1995), "Effects of the *obese* Gene Product on Body Weight Regulation in *ob/ob* Mice", Science 269:540-543.
*Remington's Pharmaceutical Sciences*, 18th Ed. (1990, Mack Publishing Co., Easton, PA 18042) pp. 1435-1712.
Rentsch et al. (1995), "Recombinant Ob-Gene Product Reduces Food Intake in Fasted Mice", *Biochem. Biophys. Res. Comm.* 214(1):131-136.
Sambrook et al., *Molecular Cloning: A Laboratory Manual*, 2d Edition (1989, Cold Spring Harbor Laboratory Press, Cold Spring Harbor, NY).
Sanders (1990), "Protein Production by Genetically Engineered Mammalian Cell Lines", *Animal Cell Biotechnology* 4:16-70.

(Continued)

*Primary Examiner*—Christine J Saoud
*Assistant Examiner*—Jegatheesan Seharaseyon

(57) ABSTRACT

The present invention provides methods and compositions for treating excess weight by administering OB protein in a form for constant supply, at a dosage of less than or equal to about 1 mg protein/kg body weight/day. Compositions and methods used for production of recombinant murine and human OB protein are also provided. Compositions and methods for preparing recombinant murine methionyl OB protein and recombinant human methionyl OB protein, including DNA sequences, vectors, host cells, methods of fermentation, and methods of purification are provided herein.

9 Claims, No Drawings

OTHER PUBLICATIONS

Sinha et al. (1996), "Nocturnal Rise of Leptin in Lean, Obese, and Non-Insulin-dependent Diabetes Mellitus Subjects", *J. Clin. Invest.* 97(5):1344-1347.

Sinha et al. (1996), "Evidence of Free and Bound Leptin in Human Circulation", *J. Clin. Invest.* 98(6):1277-1282.

Trayhurn et al. (1995), "Effects of fasting and refeeding on *ob* gene expression in white adipose tissue of lean and obese (*ob/ob*) mice", *FEBS Letters* 368:488-490.

Weigle (1994), "Appetite and the regulation of body composition", *FASEB J.* 8:302-310.

Weigle et al. (1995), "Recombinant *ob* Protein Reduces Feeding and Body Weight in the *ob/ob* Mouse", *J. Clin. Invest.* 96:2065-2070.

Zhang et al. (1994), "Positional cloning of the mouse *obese* gene and its human homologue", *Nature* 372:425-432.

Zhang et al. (1995), "Correction: Positional cloning of the mouse *obese* gene and its human homologue", *Nature* 374:479.

Cardamone et al., "Comparing the refolding and reoxidation of recombinant porcine growth hormone from a urea denatured state from *Escherichia coli* inclusion bodies," Biochemistry, 1995, vol. 34, pp. 5773-5794.

Hellman et al., In vitro refolding of cyclomaltdextrin glucanotransferase from cytoplasmic inclusion bodies formed upon expression in *Eschericia coli*, Protein Expression and Purification, 1995, vol. 6, pp. 56-62.

Kwon et al., "Refolding of a1-antitrypsin expressed as inclusion bodies in *Escherichia coli*: characterization of aggregation," Biochemica et Biophysica Acta, 1995, vol. 1247, pp. 179-184.

Lehninger, A.L., Part 1: The molecular components of cells, in Biochemistry: The Molecular Basis of Cell Strucure and Function, Copyright 1970, 1975 (Third printing 1977), p. 60, Worth Publishers, Inc., New York, NY, U.S.A.

Puri et al., "Solubilization of growth hormone and other recombinant proteins from *Escherichia coli* inclusion bodies by using a cationic surfactant", Biochem. J., 1992, vol. 285, pp. 871-879.

Blond-Elguindi et al., "Renaturation of guanidine-unfolded tryptophan synthase by multi-mixing stopped-flow dilution in D2O", FEBS Letters, vol. 241(1,2), p. 251-256 (Dec. 1988).

* cited by examiner

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 491 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 1:

```
TCTAGATTTG AGTTTTAACT TTTAGAAGGA GGAATAACAT ATGGTACCGA TCCAGAAAGT      60

TCAGGACGAC ACCAAAACCT TAATTAAAAC GATCGTTACG CGTATCAACG ACATCAGTCA     120

CACCCAGTCG GTCTCCGCTA ACAGCGTGT TACCGGTCTG GACTTCATCC CGGGTCTGCA     180

CCCGATCCTA AGCTTGTCCA AAATGGACCA GACCCTGGCT GTATACCAGC AGGTGTTAAC     240

CTCCCTGCCG TCCCAGAACG TTCTTCAGAT CGCTAACGAC CTCGAGAACC TTCGCGACCT     300

GCTGCACCTG CTGGCATTCT CCAAATCCTG CTCCCTGCCG CAGACCTCAG GTCTTCAGAA     360

ACCGGAATCC CTGGACGGGG TCCTGGAAGC ATCCCTGTAC AGCACCGAAG TTGTTGCTCT     420

GTCCCGTCTG CAGGGTTCCC TTCAGGACAT CCTTCAGCAG CTGGACGTTT CTCCGGAATG     480

TTAATGGATC C                                                          491
```

(2) INFORMATION FOR SEQ ID NO: 2:

(i) SEQUENCE CHARACTERISTICS:
       (A) LENGTH: 491 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 2:

```
AGATCTAAAC TCAAAATTGA AAATCTTCCT CCTTATTGTA TACCATGGCT AGGTCTTTCA      60

AGTCCTGCTG TGGTTTTGGA ATTAATTTTG CTAGCAATGC GCATAGTTGC TGTAGTCAGT     120

GTGGGTCAGC CAGAGGCGAT TGTCGCACA ATGGCCAGAC TGAAGTAGG GCCCAGACGT      180

GGGCTAGGAT TCGAACAGGT TTTACCTGGT CTGGGACCGA CATATGGTCG TCCACAATTG     240

GAGGGACGGC AGGGTCTTGC AAGAAGTCTA GCGATTGCTG GAGCTCTTGG AAGCGCTGGA     300

CGACGTGGAC GACCGTAAGA GGTTTAGGAC GAGGGACGGC GTCTGGAGTC CAGAAGTCTT     360

TGGCCTTAGG GACCTGCCCC AGGACCTTCG TAGGGACATG TCGTGGCTTC AACAACGAGA     420

CAGGGCAGAC GTCCCAAGGG AAGTCCTGTA GGAAGTCGTC GACCTGCAAA GAGGCCTTAC     480

AATTACCTAG G                                                          491
```

(2) INFORMATION FOR SEQ ID NO: 3:

(i) SEQUENCE CHARACTERISTICS:
       (A) LENGTH: 147 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 3:

```
Met Val Pro Ile Gln Lys Val Gln Asp Asp Thr Lys Thr Leu Ile Lys
1               5                   10                  15
Thr Ile Val Thr Arg Ile Asn Asp Ile Ser His Thr Gln Ser Val Ser
            20                  25                  30
Ala Lys Gln Arg Val Thr Gly Leu Asp Phe Ile Pro Gly Leu His Pro
        35                  40                  45
Ile Leu Ser Leu Ser Lys Met Asp Gln Thr Leu Ala Val Tyr Gln Gln
    50                  55                  60
Val Leu Thr Ser Leu Pro Ser Gln Asn Val Leu Gln Ile Ala Asn Asp
65                  70                  75                  80
Leu Glu Asn Leu Arg Asp Leu Leu His Leu Leu Ala Phe Ser Lys Ser
                85                  90                  95
Cys Ser Leu Pro Gln Thr Ser Gly Leu Gln Lys Pro Glu Ser Leu Asp
            100                 105                 110
Gly Val Leu Glu Ala Ser Leu Tyr Ser Thr Glu Val Val Ala Leu Ser
        115                 120                 125
Arg Leu Gln Gly Ser Leu Gln Asp Ile Leu Gln Gln Leu Asp Val Ser
    130                 135                 140
Pro Glu Cys
145
```

(2) INFORMATION FOR SEQ ID NO: 4:

(i) SEQUENCE CHARACTERISTICS:
        (A) LENGTH: 454 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 4:

```
CATATGGTAC CGATCCAGAA AGTTCAGGAC GACACCAAAA CCTTAATTAA AACGATCGTT    60
ACGCGTATCA ACGACATCAG TCACACCCAG TCGGTGAGCT CTAAACAGCG TGTTACAGGC   120
CTGGACTTCA TCCCGGGTCT GCACCCGATC CTGACCTTGT CCAAAATGGA CCAGACCCTG   180
GCTGTATACC AGCAGATCTT AACCTCCATG CCGTCCCGTA ACGTTCTTCA GATCTCTAAC   240
GACCTCGAGA ACCTTCGCGA CCTGCTGCAC GTGCTGGCAT TCTCCAAATC CTGCCACCTG   300
CCATGGGCTT CAGGTCTTGA GACTCTGGAC TCTCTGGGCG GGTCCTGGA AGCATCCGGT    360
TACAGCACCG AAGTTGTTGC TCTGTCCCGT CTGCAGGGTT CCCTTCAGGA CATGCTTTGG   420
CAGCTGGACC TGTCTCCGGG TTGTTAATGG ATCC                               454
```

(2) INFORMATION FOR SEQ ID NO: 5:

(i) SEQUENCE CHARACTERISTICS:
        (A) LENGTH: 454 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 5:

```
GTATACCATG GCTAGGTCTT TCAAGTCCTG CTGTGGTTTT GGAATTAATT TTGCTAGCAA    60
TGCGCATAGT TGCTGTAGTC AGTGTGGGTC AGCCACTCGA GATTTGTCGC ACAATGTCCG   120
```

```
                                    -continued

GACCTGAAGT AGGGCCCAGA CGTGGGCTAG GACTGGAACA GGTTTTACCT GGTCTGGGAC    180

CGACATATGG TCGTCTAGAA TTGGAGGTAC GGCAGGGCAT TGCAAGAAGT CTAGAGATTG    240

CTGGAGCTCT TGGAAGCGCT GGACGACGTG CACGACCGTA AGAGGTTTAG GACGGTGGAC    300

GGTACCCGAA GTCCAGAACT CTGAGACCTG AGAGACCCGC CCCAGGACCT TCGTAGGCCA    360

ATGTCGTGGC TTCAACAACG AGACAGGGCA GACGTCCCAA GGGAAGTCCT GTACGAAACC    420

GTCGACCTGG ACAGAGGCCC AACAATTACC TAGG                                454

(2) INFORMATION FOR SEQ ID NO: 6:

(i) SEQUENCE CHARACTERISTICS:
            (A) LENGTH: 147 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 6:

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Arg Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Leu Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145
```

US 7,524,940 B2

OB PROTEIN COMPOSITIONS AND METHODS

CROSS-REFERENCE TO RELATED APPLICATIONS

This application is a continuation of U.S. patent application Ser. No. 09/366,133, filed on Aug. 2, 1999, now abandoned; which is a continuation of U.S. patent application Ser. No. 08/920,608, filed on Aug. 27, 1997, now abandoned; which is a continuation of U.S. patent application Ser. No. 08/474,833, filed Jun. 7, 1995, now abandoned, the contents of which are hereby incorporated by reference in their entirety.

FIELD OF THE INVENTION

The present invention relates to OB protein compositions and methods for preparation and use thereof.

BACKGROUND

Although the molecular basis for obesity is largely unknown, the identification of the "OB gene" and protein encoded by ("OB protein") has shed some light on mechanisms the body uses to regulate body fat deposition. Zhang et al., Nature 372: 425-432 (1994); see also, the Correction at Nature 374: 479 (1995). The OB protein has been demonstrated to be active in vivo in both ob/ob mutant mice (mice obese due to a defect in the production of the OB gene product) as well as in normal, wild type mice. The biological activity manifests itself in, among other things, weight loss. To date, however, optimum conditions for obtaining the rapid weight loss in normal animals has not been ascertained. In fact, some studies have shown that, when administered by injection, rather large dosages (10 mg of recombinant murine protein/kg body weight/day) are necessary for normal mice to lose 2.6% of their body weight (at the end of a 32 day period). While presently uncertain, one explanation for the necessity of such large dosages is that the optimum weight loss effects are seen predominantly when the protein is in constant circulation, a condition that may not be efficiently achieved by injecting the protein.

SUMMARY OF THE INVENTION

The present invention stems from the observation that, as compared to administering OB protein by injection, administering OB protein by continuous pump infusion results in equivalent (or better) weight loss, in a shorter time, and with substantially lower dosages. The working example below demonstrates that a dose of 0.5 mg protein/kg body weight/day, administered via implantable osmotic pump, results in a weight loss of over 4% (as compared to baseline weight). This is in substantial contrast to other studies where similar, or less weight loss (at a comparable time point) was observed with intraperitoneal injection at the relatively high dosage of 10 mg of protein/kg body weight/day.

Thus, one aspect of the present invention is a method of treating excess weight by administering OB protein in a form for constant supply, at a dosage of less than or equal to about 1 mg protein/kg body weight/day. The dosage of less than or equal to about 1 mg protein/kg/day refers to dosages sufficient to result in observable weight loss. This is apparent from the present studies where a dosage of 0.5 mg/kg/day was sufficient to result in observable weight loss when continuously administered. In studies where injection had been the mode of administration, far higher dosages were required for weight loss. At injection dosages of 0.1 and 1 mg/kg/day, substantially no weight loss was observed in wild type (normal) mice. For example, in one study, at a comparable time point (6th day), there was a 0.2% loss at the 1 mg/kg dose (data not shown). Minimal weight loss was observed at the relatively high 10 mg/kg/day dose. (1.9% weight loss at day 6, data not shown). Thus, the present invention provides for dosages of 1 mg/kg/day or less when administered so that the supply of protein is continuous.

Connected with the present studies are the compositions and methods used for production of recombinant murine and human OB protein. The first example below discloses the preparation of recombinant murine protein, and the second example below discloses the preparation of recombinant human protein.

Additional aspects of the present invention, therefore, include the below compositions and methods for preparing recombinant murine methionyl OB protein and recombinant human methionyl OB protein, including DNA sequences, vectors, host cells, methods of fermentation, and methods of purification.

DETAILED DESCRIPTION

The present invention stems from the observation that continuous administration of OB protein results in the need for much lower dosages for weight loss than those dosages required by acute daily injection. As set forth above, a dosage of 1 mg protein/kg body weight/day or less, continuously administered, resulted in rapid weight loss. When the underivatized protein was administered by acute injection at the 1 mg/kg/day dose, almost no weight loss in wild type (normal) mice.

The OB protein may be selected from the recombinant murine and human methionyl proteins set forth below (SEQ. ID Nos. 3 and 6) or those lacking a glutaminyl residue at position 28. (See Zhang et al, Nature, supra, at page 428.) The recombinant human OB gene product is, as a mature protein, 146 amino acids; some of the DNAs obtained were observed to encode a protein lacking a glurarnine residue at position 28. Zhang et al., Nature 372 at 428. The murine protein is substantially homologous to the human protein, particularly as a mature protein, and, further, particularly at the N-terminus. One may prepare an analog of the recombinant human protein by altering (such as substituting amino acid residues), in the recombinant human sequence, the amino acids which diverge from the murine sequence. Because the recombinant human protein has biological activity in mice, such analog would likely be active. Proteins lacking an N-terminal methionyl residue, such as those produced by eukaryotic expression, are also available for use.

In addition, although the present working example involved continuous administration via implantable pump, it is contemplated that other modes of continuous administration may be practiced. For example, chemical derivatization may result in sustained release forms of the protein which have the effect of continuous presence in the blood stream, in predictable amounts. Thus, one may derivatize the above proteins to effectuate such continuous administration. The dosage of 1 mg protein/kg body weight/day or less herein refers to the mass of protein, exclusive of other chemical moieties used to derivatize the protein.

Generally, the present protein (herein the term "protein" is used to include "peptide", unless otherwise indicated) may be derivatized by the attachment of one or more chemical moieties to the protein moiety. The chemically modified derivatives may be further formulated for intraarterial, intraperitoneal, intramuscular subcutaneous, intravenous, oral, nasal, pulmonary, topical or other routes of administration. Chemical modification of biologically active proteins has been found to provide additional advantages under certain circumstances, such as increasing the stability and circulation time of the therapeutic protein and decreasing immunogenicity. See U.S. Pat. No. 4,179,337, Davis et al., issued Dec. 18, 1979. For a review, see Abuchowski et al., in Enzymes as Drugs. (J. S. Holcerberg and J. Roberts, eds. pp. 367-383 (1981)). A review article describing protein modification and fusion proteins is Francis, Focus on Growth Factors 3: 4-10 (May 1992) (published by Mediscript, Mountview Court, Friern Barnet Lane, London N20, 0LD, UK). For the present continuous administration, it is preferred that the chemical modification allow for an increase in circulation time of the protein, so that a dosage of about 1 mg protein (exclusive of chemical moiety)/kg body weight of a mammal/day or less will result in weight loss of a mammal. The present continuous administration will provide for weight loss of approximately 5% of body mass in a period of 7 or fewer days.

The chemical moieties suitable for derivatization may be selected from among water soluble polymers. The polymer selected should be water soluble so that the protein to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For the present proteins and peptides, the effectiveness of the derivatization may be ascertained by administering the derivative, in the desired form (i.e., by osmotic pump, or, more preferably, by injection or infusion, or, further formulated for oral, pulmonary or nasal delivery, for example), and measuring weight loss.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. E.g., EP 0 401 384 herein incorporated by reference (coupling PEG to G-CSF), see also Malik et al., Exp. Hematol. 20: 1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the $pK_a$ differences between the ε-amino group of the lysine residues and that of the α-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

In yet another aspect of the present invention, provided are methods of using pharmaceutical compositions of the proteins and derivatives. Such pharmaceutical compositions may be for administration for injection, or for oral, pulmonary, nasal or other forms of administration which allow for the desired circulating dose of about 1 mg protein/kg body weight/day or less. In general, comprehended by the invention are pharmaceutical compositions comprising effective amounts of protein or derivative products of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. The effective amounts are those herein described.

The OB proteins and derivatives described are useful for modulation of the rate or quantity of fat cell deposition in a mammal. This is thought to be accomplished, in part, by a reduction in appetite, i.e., a reduction in food intake. Thus, one observable result is weight loss, or, put another way, a method of treating excess weight (via weight loss). Thus, the present compositions are useful for the manufacture of a medicament for treating excess weight in a mammal. Another aspect is a method for reducing appetite. Either of these aspects, modulation of fat deposition or modulation of appetite, are particularly important treatments for humans (or other mammals) who desire to lose weight.

One skilled in the art will be able to ascertain other effective dosages by administration and observing weight loss. Here, the dosage of 1 mg protein/kg body weight/day or less was seen to be particularly effective, when administered on a continuous basis. More particularly, the dosage of 0.5 mg/kg body weight/day was seen to be particularly effective on normal mice. Excess weight refers to body mass for which removal is desired. It is contemplated that the present compositions and methods will be used to treat cases where removal of such excess weight (as a result of the present invention) will benefit other health concerns, such as diabetes, high blood pressure or cardiac problems, high cholesterol levels, low locomotion levels and other manifestations of excess weight. As such, the present compositions and methods may be used in conjunction with other medicaments, such as those useful for the treatment of diabetes (e.g., insulin, and possibly amylin), cholesterol and blood pressure lowering medicaments, and locomotion increasing medicaments (e.g., amphetamines). Such administration may be simultaneous or may be in serriatim.

In addition, the present compositions and methods may be used in conjunction with surgical procedures, such as cosmetic surgeries designed to alter the overall appearance of a body (e.g., liposuction or laser surgeries designed to reduce body mass). The health benefits of cardiac surgeries may be increased with concomitant use of the present compositions and methods.

Therefore, the present invention encompasses a method of treating excess weight in a mammal by continuous administration of 1 mg protein/kg body weight/day or less of an OB protein selected from the group consisting:

(a) recombinant methionyl murine OB protein (SEQ ID No. 3);

(b) recombinant methionyl human OB protein (SEQ ID No. 6);

(c) the protein of (a) or (b) lacking the methionyl residue at position −1;

(d) the protein of (a), (b), or (c) lacking a glutamine at position 28; and (e) a chemically modified derivative of (a), (b), (c) or (d), wherein the chemical modification allows for an increase in circulation time.

Preferably, the composition of subpart (e) is a pegylated derivative, and, more preferably, an N-terminally pegylated derivative.

The derivative of subpart (e) allows for continuous administration of the protein by increasing the circulation time of the (unmodified) protein. The present invention also encompasses a method of treating excess weight where the method of continuous administration is by implantable pump, such as an osmotic pump.

In other aspects, the present invention relates to recombinant murine and recombinant human OB DNAs and proteins, such as those of SEQ. ID NOs. 1, 4, 3, and 6, below. The recombinant proteins below are bacterially expressed, and contain N-terminal methionyl residues. Vectors and host cells useful for producing such proteins are also provided. The vectors include pCFM1656 containing SEQ ID No. 1 or 4, and host cells containing such vectors.

Methods for preparation of the recombinant proteins are also provided, including methods for fermentation and methods for purification.

In particular, the use of sarcosine for refolding of OB protein in solution, obtained from bacterial inclusion bodies, provided for extremely efficient refolding. When proteins are expressed in bacteria, they may not be in the proper three-dimensional configuration, or, as referred to herein, properly refolded. The three dimensional configuration may be critical for biological activity, and storage stability. Although Sarckosyl has been used in processes for purification of another protein (G-CSF, e.g., WO 89/10932), surprisingly, the use of sarcosine for the OB protein has resulted in a refolding efficiency of over 95%. Contemplated herein is the use of N-lauroylsarcosine in a range of 0.5%-2.0% weight per volume of OB protein in solution (obtained from inclusion bodies). With the use of 1% sodium sarcosine, the refolding efficiency, as determined by SDS PAGE and reverse phase HPLC, was 95% or greater. While one skilled in the art will recognize that other compositions may be used for refolding, the use of N-lauroyl sarcosine, as illustrated in the examples below, is particularly advantageous for providing extremely efficient refolding. The removal of sarcosine was accomplished using Dowex®.

Therefore, the present invention also includes a method of refolding partially purified OB protein in a solution obtained from inclusion bodies, said partially purified OB protein selected from the group consisting of (a) recombinant methionyl murine OB protein (SEQ ID No. 3);

(b) recombinant methionyl human OB protein (SEQ ID No. 6);

(c) the protein of (a) or (b) lacking the methionyl residue at position −1;

wherein said refolding is accomplished using sarcosine.

The present invention also includes methods of wherein said N-lauroyl sarcosine is used at a concentration of 0.5%-2.0% weight per volume of solution, and, more particularly, the use of 1% N-lauroyl sarcosine. An oxidizing agent, such as copper sulfate, is also used in the refolding process.

The following examples are offered to more fully illustrate the invention, but are not to be construed as limiting the scope thereof.

EXAMPLE 1

Use of Murine OB Protein in a Continuous Pump Infusion System

This example demonstrates that continuous infusion of OB protein results in weight loss in normal mice. Normal (non-obese) mice were administered murine OB protein via osmotic pump infusion. A dosage of 0.5 mg protein/kg body weight/day resulted in a 4.62% (+/−1.34%) loss from baseline weight by the 6th day of infusion.

Materials and Methods

Animals: Wild type (+/+) C57B16 mice were used for this experiment. The age of the mice at the initial time point was 8 weeks, and the animals were weight stabilized. 10 mice were used for each cohort (vehicle vs. protein).

Animal Handling.

Feeding and weight measurement. Mice were given ground rodent chow (PMI Feeds, Inc.) in powdered food feeders (Allentown Caging and Equipment) which allowed a more accurate and sensitive measurement than use of regular block chow. Weight was measured at the same time each day (2:00 p.m.), for a period of 6 days. Body weight on the day prior to the infusion was defined as baseline weight. The mice used weighed 18-22 grams.

Housing: Mice were single-housed, and maintained under humane conditions.

Administration of Protein or Vehicle. Protein (as described below) or vehicle (phosphate buffered saline, pH 7.4) were administered by osmotic pump infusion. Alzet osmotic minipumps (Alza, Palo Alto, Calif., model no. 1007D) were surgically placed in each mice in a subcutaneous pocket in the subscapular area. The pumps were calibrated to administer 0.5 µl protein in solution per hour for a dosage of 0.5 mg protein/kg body weight/day.

Controls: Control animals were those who had a Alzet osmotic minipump infusing phosphate buffered saline (pH 7.4).

Protein: Recombinant murine OB protein was used for the present experiments, generally at a concentration of about 0.9 mg/ml phosphate buffered saline, pH 7.4. The amino acid sequence (and DNA sequence) used was the following:

```
                Recombinant murine met OB (double stranded) DNA
                and amino acid sequence: (Seq. ID. Nos. 1, 2 and 3):0

TCTAGATTTGAGTTTTAACTTTTAGAAGGAGGAATAACATATGGTACCGATCCAGAAAGT
   9-+---------+---------+---------+---------+---------+--------    68
     AGATCTAAACTCAAAATTGAAAATCTTCCTCCTTATTGTATACCATGGCTAGGTCTTTCA
                                                   M  V  P  I  Q  K  V -

TCAGGACGACACCAAAACCTTAATTAAAACGATCGTTACGCGTATCAACGACATCAGTCA
  69-+---------+---------+---------+---------+---------+--------   128
     AGTCCTGCTGTGGTTTTGGAATTAATTTTGCTAGCAATGCGCATAGTTGCTGTAGTCAGT
      Q  D  D  T  K  T  L  I  K  T  I  V  T  R  I  N  D  I  S  H -

CACCCAGTCGGTCTCCGCTAAACAGCGTGTTACCGGTCTGGACTTCATCCCGGGTCTGCA
 129-+---------+---------+---------+---------+---------+--------   188
     GTGGGTCAGCCAGAGGCGATTTGTCGCACAATGGCCAGACCTGAAGTAGGGCCCAGACGT
      T  Q  S  V  S  A  K  Q  R  V  T  G  L  D  F  I  P  G  L  H -

CCCGATCCTAAGCTTGTCCAAAATGGACCAGACCCTGGCTGTATACCAGCAGGTGTTAAC
 189-+---------+---------+---------+---------+---------+--------   248
     GGGCTAGGATTCGAACAGGTTTTACCTGGTCTGGGACCGACATATGGTCGTCCACAATTG
      P  I  L  S  L  S  K  M  D  Q  T  L  A  V  Y  Q  Q  V  L  T -

CTCCCTGCCGTCCCAGAACGTTCTTCAGATCGCTAACGACCTCGAGAACCTTCGCGACCT
 249-+---------+---------+---------+---------+---------+--------   308
     GAGGGACGGCAGGGTCTTGCAAGAAGTCTAGCGATTGCTGGAGCTCTTGGAAGCGCTGGA
      S  L  P  S  Q  N  V  L  Q  I  A  N  D  L  E  N  L  R  D  L -

GCTGCACCTGCTGGCATTCTCCAAATCCTGCTCCCTGCCGCAGACCTCAGGTCTTCAGAA
 309-+---------+---------+---------+---------+---------+--------   368
     CGACGTGGACGACCGTAAGAGGTTTAGGACGAGGGACGGCGTCTGGAGTCCAGAAGTCTT
      L  H  L  L  A  F  S  K  S  C  S  L  P  Q  T  S  G  L  Q  K -

ACCGGAATCCCTGGACGGGGTCCTGGAAGCATCCCTGTACAGCACCGAAGTTGTTGCTCT
 369-+---------+---------+---------+---------+---------+--------   428
     TGGCCTTAGGGACCTGCCCCAGGACCTTCGTAGGGACATGTCGTGGCTTCAACAACGAGA
      P  E  S  L  D  G  V  L  E  A  S  L  Y  S  T  E  V  V  A  L -

GTCCCGTCTGCAGGGTTCCCTTCAGGACATCCTTCAGCAGCTGGACGTTTCTCCGGAATG
 429-+---------+---------+---------+---------+---------+--------   488
     CAGGGCAGACGTCCCAAGGGAAGTCCTGTAGGAAGTCGTCGACCTGCAAAGAGGCCTTAC
      S  R  L  Q  G  S  L  Q  D  I  L  Q  Q  L  D  V  S  P  E  C -

TTAATGGATCC
 489-+---------
```

-continued

Recombinant murine met OB (double stranded) DNA
and amino acid sequence: (Seq. ID. Nos. 1, 2 and 3):0

AATTACCTAGG

Herein, the first amino acid of the amino acid sequence for recombinant protein is referred to as +1, and is valine, and the amino acid at position-1 is methionine. The C-terminal amino acid is number 146 (cysteine).

The cloning of the murine OB DNA for expression in *E. coli* was done as follows. The DNA sequence was deduced from the published peptide sequence that appeared in Zhang et al., Nature 372:425-432 (1994). It was reverse translated using *E. coli* optimal codons. The terminal cloning sites were XbaI to BamHI. A ribosomal binding enhancer and a strong ribosomal binding site were included in front of the coding region. The duplex DNA sequence was synthesized using standard techniques. Correct clones were confirmed by demonstrating expression of the recombinant protein and presence of the correct OB DNA sequence in the resident plasmid.

Expression Vector and Host Strain

The plasmid expression vector used was pCFM1656, ATCC Accession No. 69576. The above DNA was ligated into the expression vector pCFM1656 which had been linearized with XbaI and BamHI and transformed into the *E. coli* host strain, FM5. *E. coli* FM5 cells were derived at Amgen Inc., Thousand Oaks, Calif. from *E. coli* K-12 strain (Bachmann, et al., Bacteriol. Rev. 40: 116-167 (1976)) and contain the integrated lambda phage repressor gene, $cI_{857}$ (Sussman et al., C.R. Acad. Sci. 254: 1517-1579 (1962)). Vector production, cell transformation, and colony selection were performed by standard methods. E.g., Sambrook, et al., Molecular Cloning: A Laboratory Manual, 2d Edition, Cold Spring Harbor Laboratory Press, Cold Spring Harbor, N.Y. Host cells were grown in LB media.

Fermentation Process A three-phase fermentation protocol was used known as a fed-batch process. Media compositions are set forth below.

Batch: A nitrogen and phosphate source were sterilized (by raising to 122° C. for 35 minutes, 18-20 psi) in the fermentation vessel (Biolafitte, 12 liter capacity). Upon cooling, carbon, magnesium, vitamin, and trace metal sources were added aseptically. An overnight culture of the above recombinant murine protein-producing bacteria (16 hours or more) of 500 mL (grown in LB broth) was added to the fermentor.

Feed I: Upon reaching between 4.0-6.0 $OD_{600}$, cultures were fed with Feed I. The glucose was fed at a limiting rate in order to control the growth rate (μ). An automated system (called the Distributive Control System) was instructed to control the growth rate to 0.15 generations per hour.

Feed II: When the OD600 had reached 30, culture temperature was slowly increased to 42° C. and the feed was changed to Feed II, below. The fermentation was then allowed to continue for 10 hours with sampling every 2 hours. After 10 hours, the contents of the fermentor was chilled to below 20° C. and harvested by centrifugation.

| Media Composition: | | |
|---|---|---|
| Batch: | 10 g/L | Yeast extract |
| | 5.25 g/L | $(NH_4)_2SO_4$ |

-continued

| Media Composition: | | |
|---|---|---|
| | 3.5 g/L | $K_2HPO_4$ |
| | 4.0 g/L | $KH_2PO_4$ |
| | 5.0 g/L | Glucose |
| | 1.0 g/L | $MgSO_4 \cdot 7H_2O$ |
| | 2.0 mL/L | Vitamin Solution |
| | 2.0 mL/L | Trace Metal Solution |
| | 1.0 mL/L | P2000 Antifoam |
| Feed I: | 50 g/L | Bacto-tyrptone |
| | 50 g/L | Yeast extract |
| | 450 g/L | Glucose |
| | 8.75 g/L | $MgSO_4 \cdot 7H_2O$ |
| | 10 mL/L | Vitamin Solution |
| | 10 mL/L | Trace Metal Solution |
| Feed II: | 200 g/L | Bacto-tryptone |
| | 100 g/L | Yeast extract |
| | 110 g/L | Glucose |

Vitamin Solution (Batch and Feed I):

0.5 g Biotin, 0.4 g Folic acid, and 4.2 g riboflavin, were dissolved in 450 mls $H_2O$ and 3 mls 10 N NaOH, and brought to 500 mls in $H_2O$. 14 g pyridoxine-HCl and 61 g niacin were dissolved 150 ml $H_2O$ and 50 ml 10 N NaOH, and brought to 250 ml in $H_2O$. 54 g pantothenic acid was dissolved in 200 ml $H_2O$, and brought to 250 ml. The three solutions were combined and brought to 10 liters total volume.

Trace Metal Solution (Batch and Feed I):

Ferric Chloride ($FeCl_3 \cdot 6H_2O$): 27 g/L
Zinc Chloride ($ZnCl_2 \cdot 4H_2O$): 2 g/L
Cobalt Chloride ($CoCl_2 \cdot 6H_2O$): 2 g/L
Sodium Molybdate ($NaMoO_4 \cdot 2H_2O$): 2 g/L
Calcium Chloride ($CaCl_2 \cdot 2H_2O$): 1 g/L
Cupric Sulfate ($CuSO_4 \cdot 5H_2O$): 1.9 g/L
Boric Acid ($H_3BO_3$): 0.5 g/L
Manganese Chloride ($MnCl_2 \cdot 4H_2O$): 1.6 g/L
Sodium Citrate dihydrate: 73.5 g/L Purification Process for Murine OB Protein Purification was accomplished by the following steps (unless otherwise noted, the following steps were performed at 4° C.):

1. Cell paste. *E. coli* cell paste was suspended in 5 times volume of 7 mM of EDTA, pH 7.0. The cells in the EDTA were further broken by two passes through a microfluidizer. The broken cells were centrifuged at 4.2 K rpm for 1 hour in a Beckman J6-B centrifuge with a JS-4.2 rotor.

2. Inclusion body wash #1. The supernatant from above was removed, and the pellet was resuspended with 5 times volume of 7 mM EDTA, pH 7.0, and homogenized. This mixture was centrifuged as in step 1.

3. Inclusion body wash #2. The supernatant from above was removed, and the pellet was resuspended in ten times volume of 20 mM tris, pH 8.5, 10 mM DTT, and 1% deoxycholate, and homogenized. This mixture was centrifuged as in step 1.

4. Inclusion body wash #3. The supernatant from above was removed and the pellet was resuspended in ten times volume of distilled water, and homogenized. This mixture was centrifuged as in step 1.

5. Refolding. The pellet was refolded with 15 volumes of 10 mM HEPES, pH 8.5, 1% sodium sarcosine (N-lauroyl sarcosine), at room temperature. After 60 minutes, the solution is made to be 60 µM copper sulfate, and then stirred overnight.

6. Removal of sarcosine. The refolding mixture was diluted with 5 volumes of 10 mM tris buffer, pH 7.5, and centrifuged as in step 1. The supernatant was collected, and mixed with agitation for one hour with Dowex® 1-X4 resin (Dow Chemical Co., Midland Mich.), 20-50 mesh, chloride form, at 0.066% total volume of diluted refolding mix. See WO 89/10932 at page 26 for more information on Dowex®. This mixture was poured into a column and the eluant was collected. Removal of sarcosine was ascertained by reverse phase HPLC.

7. Acid precipitation. The eluant from the previous step was collected, and pH adjusted to pH 5.5, and incubated for 30 minutes at room temperature. This mixture was centrifuged as in step 1.

8. Cation exchange chromatography. The pH of the supernatant from the previous step was adjusted to pH 4.2, and loaded on CM Sepharose Fast Flow (at 7% volume). 20 column volumes of salt gradient were done at 20 mM NaOAC, pH 4.2, 0 M to 1.0 M NaCl.

9. Hydrophobic interaction chromatography. The CM Sepharose pool of peak fractions (ascertained from ultraviolet absorbance) from the above step was made to be 0.2 M ammonium sulfate. A 20 column volume reverse salt gradient was done at 5 mM NaOAC, pH 4.2, with 0.4 M to 0 M ammonium sulfate. This material was concentrated and diafiltered into PBS.

Results

Presented below are the percent (%) differences from baseline weight in C57B16J mice (8 weeks old):

TABLE 1

Weight Loss Upon Continuous Infusion

| Time (days) | Vehicle (PBS) | Recombinant OB protein |
|---|---|---|
| Days 1-2 | 3.24 +/− 1.13 | 1.68 +/− 1.4 |
| Days 3-4 | 4.3 +/− .97 | −2.12 +/− .79 |
| Days 5-6 | 4.64 +/− .96 | −4.62 +/− 1.3 |

As can be seen, at the end of a 6 day continuous infusion regime, animals receiving the OB protein lost over 4% of their body weight, as compared to baseline. This is a substantially more rapid weight loss than has been observed with intraperitoneal (i.p.) injection. Weight loss at the end of a 32-day injection period, in wild type (normal) mice, with daily i.p. injections of recombinant murine OB protein at a 10 mg/kg dose was 2.6%, and had not been more than 4% at any time during the dosing schedule (data not shown). The present data indicate that with continuous infusion, a 20-fold lower dosage (0.5 mg/kg vs. 10 mg/kg) achieves more weight loss in a shorter time period.

The results seen here are statistically significant, e.g., −4.62% with $p<0.0001$.

EXAMPLE 2

Dose Response Studies

An additional study demonstrated that there was a dose response to continuous administration of OB protein. In this study, non-obese, CD-1 mice, weighing 35-40 g were administered recombinant murine OB protein using methods similar to the above example. The results are set forth in Table 2, below, (with % body weight lost as compared to baseline, measured as above):

TABLE 2

Dose Response With Continuous Administration

| Dose | Time | % Reduction in body weight |
|---|---|---|
| 0.03 mg/kg/day | Day 2 | 3.5 |
| 1 mg/kg/day | Day 2 | 7.5 |
| 1 mg/kg/day | Day 4 | 14 |

As can be seen, increasing the dose from 0.03 mg/kg/day to 1 mg/kg/day increased the weight lost from 3.5% to 7.5%. It is also noteworthy that at day 4, the 1 mg/kg/day dosage resulted in a 14% reduction in body weight.

EXAMPLE 3

Cloning and Expression of a Recombinant Human Methionyl OB Protein

This example provides compositions and methods for preparation of a recombinant human version of the OB protein.

The human version of the OB DNA was constructed from the murine OB DNA, as in Example 1, above, by replacing the region between the MluI and BamHI sites with duplex DNA (made from synthetic oligonucleotides) in which 20 codon substitutions had been designed. The MluI site is shown under the solid line in the sequence below. This DNA was put into the pCFM1656 vector (ATCC Accession No. 69576), in the same fashion as the recombinant murine protein, as described above. Herein, the first amino acid of the amino acid sequence for recombinant human protein below is referred to as +1, and is valine, and the amino acid at position −1 is methionine. The C-terminal amino acid is number 146 (cysteine).

Recombinant human met OB (Double Stranded) DNA
and amino acid sequence: (Seq. ID. Nos. 4, 5 and 6)

CATATGGTACCGATCCAGAAAGTTCAGGACGACACCAAAACCTTAATTAAAACGATCGTT

-continued

Recombinant human met OB (Double Stranded) DNA
and amino acid sequence: (Seq. ID. Nos. 4, 5 and 6)

```
1---------+---------+---------+---------+---------+---------+  60
  GTATACCATGGCTAGGTCTTTCAAGTCCTGCTGTGGTTTTGGAATTAATTTTGCTAGCAA
      M  V  P  I  Q  K  V  Q  D  D  T  K  T  L  I  K  T  I  V  -

ACGCGTATCAACGACATCAGTCACACCCAGTCGGTGAGCTCTAAACAGCGTGTTACAGGC
61---------+---------+---------+---------+---------+---------+ 120
  TGCGCATAGTTGCTGTAGTCAGTGTGGGTCAGCCACTCGAGATTTGTCGCACAATGTCCG
   T  R  I  N  D  I  S  H  T  Q  S  V  S  S  K  Q  R  V  T  G  -

CTGGACTTCATCCCGGGTCTGCACCCGATCCTGACCTTGTCCAAAATGGACCAGACCCTG
121---------+---------+---------+---------+---------+---------+ 180
    GACCTGAAGTAGGGCCCAGACGTGGGCTAGGACTGGAACAGGTTTTACCTGGTCTGGGAC
     L  D  F  I  P  G  L  H  P  I  L  T  L  S  K  M  D  Q  T  L  -

GCTGTATACCAGCAGATCTTAACCTCCATGCCGTCCCGTAACGTTCTTCAGATCTCTAAC
181---------+---------+---------+---------+---------+---------+ 240
    CGACATATGGTCGTCTAGAATTGGAGGTACGGCAGGGCATTGCAAGAAGTCTAGAGATTG
     A  V  Y  Q  Q  I  L  T  S  M  P  S  R  N  V  L  Q  I  S  N  -

GACCTCGAGAACCTTCGCGACCTGCTGCACGTGCTGGCATTCTCCAAATCCTGCCACCTG
241---------+---------+---------+---------+---------+---------+ 300
    CTGGAGCTCTTGGAAGCGCTGGACGACGTGCACGACCGTAAGAGGTTTAGGACGGTGGAC
     D  L  E  N  L  R  D  L  L  H  V  L  A  F  S  K  S  C  H  L  -

CCATGGGCTTCAGGTCTTGAGACTCTGGACTCTCTGGGCGGGGTCCTGGAAGCATCCGGT
301---------+---------+---------+---------+---------+---------+ 360
    GGTACCCGAAGTCCAGAACTCTGAGACCTGAGAGACCCGCCCCAGGACCTTCGTAGGCCA
     P  W  A  S  G  L  E  T  L  D  S  L  G  G  V  L  E  A  S  G  -

TACAGCACCGAAGTTGTTGCTCTGTCCCGTCTGCAGGGTTCCCTTCAGGACATGCTTTGG
361---------+---------+---------+---------+---------+---------+ 420
    ATGTCGTGGCTTCAACAACGAGACAGGGCAGACGTCCCAAGGGAAGTCCTGTACGAAACC
     Y  S  T  E  V  V  A  L  S  R  L  Q  G  S  L  Q  D  M  L  W  -

CAGCTGGACCTGTCTCCGGGTTGTTAATGGATCC
421---------+---------+---------+----  454
    GTCGACCTGGACAGAGGCCCAACAATTACCTAGG
     Q  L  D  L  S  P  G  C  *
```

Fermentation: Fermentation of the above host cells to produce recombinant human OB protein was accomplished using the conditions and compositions as described above for recombinant murine material. The results were analyzed for yield (grams ob DNA product/liter of fermentation broth), prior to purification of the recombinant human OB material. (Minor amounts of bacterial protein were present.) Bacterial expression was also calculated.

TABLE 3

Analysis of Human OB Protein Expression

| Timepoint | OD (@ 600 nm) | Yield (g/L) | Expression (mg/OD · L) |
|---|---|---|---|
| Ind. + 2 hours. | 47 | 1.91 | 41 |
| Ind. + 4 hours. | 79 | 9.48 | 120 |
| Ind. + 6 hours. | 95 | 13.01 | 137 |
| Ind. + 8 hours. | 94 | 13.24 | 141 |
| Ind. + 10 hours. | 98 | 14.65 | 149 | abbreviations: Ind. +_____ hours means the hours after induction of protein expression, as described in Example I for the recombinant murine material using pCFM1656

OD: optical density, as measured by spectrophotometer 20 milligrams per OD unit per liter mg/OD-L: expression in terms of milligrams of protein per OD unit per liter.

g/L: grams protein/liter fermentation broth

Purification of the recombinant human OB protein: Recombinant human protein may be purified using methods similar to those used for purification of recombinant murine protein, as in Example 1, above. For preparation of recombinant human OB protein, step 8 was performed by adjusting the pH of the supernatant from step 7 to pH 5.0, and loading this onto a CM Sepharose fast flow column. The 20 column volume salt gradient was performed at 20 mM NaOAC, pH 5.5, 0M to 0.5 M NaCl. Step 9 was performed by diluting the CM Sepharose pool four fold with water, and adjusting the pH to 7.5. This mixture was made to 0.7 M ammonium sulfate. Twenty column volume reverse salt gradient was done at 5 mM NaOAC, pH 5.5, 0.2 M to 0 M ammonium sulfate. Otherwise, the above steps were identical.

While the present invention has been described in terms of preferred embodiments, it is understood that variations and modifications will occur to those skilled in the art. Therefore, it is intended that the appended claims cover all such equivalent variations which come within the scope of the invention as claimed.

The invention claimed is:

1. A method of properly refolding partially purified OB protein obtained from inclusion bodies, said partially purified OB protein selected from the group consisting of:
   (a) recombinant methionyl murine OB protein (SEQ ID NO: 3);
   (b) recombinant methionyl human OB protein (SEQ ID NO: 6);
   (c) the protein of (a) or (b) lacking the methionyl residue at position –1;
   wherein said refolding is accomplished by a method comprising contacting said protein with N-lauroyl sarcosine, wherein said contacting effects a proper three-dimensional configuration of said OB protein.

2. The method of claim 1 wherein said N-lauroyl sarcosine is used at a concentration of 0.5%-2.0% weight per volume of solution.

3. The method of claim 2 wherein said N-lauroyl sarcosine is used at a concentration of 1.0% weight per volume of solution.

4. The method of claim 1, wherein said contacting further comprises effecting a refolding efficiency of greater than 95% as determined by SDS PAGE or reverse phase HPLC.

5. The method of claim 1, wherein said contacting further comprises effecting a refolding efficiency of greater than 95% as determined by SDS PAGE or reverse phase HPLC.

6. A method of properly refolding partially purified OB protein obtained from inclusion bodies, said partially purified OB protein selected from the group consisting of:
   (a) recombinant methionyl murine OB protein (SEQ ID NO: 3);
   (b) recombinant methionyl human OB protein (SEQ ID NO: 6);
   (c) the protein of (a) or (b) lacking the methionyl residue at position –1;

wherein said refolding is accomplished by a method comprising contacting said protein with N-lauroyl sarcosine and an oxidizing agent, wherein said contacting effects a proper three-dimensional configuration of said OB protein.

7. The method of claim 6 wherein said oxidizing agent is copper sulfate.

8. The method of claim 7 wherein said N-lauroyl sarcosine is used at a concentration of 1.0% weight per volume of solution.

9. The method of claim 6 wherein said N-lauroyl sarcosine is used at a concentration of 0.5%-2.0% weight per volume of solution.

\* \* \* \* \*

UNITED STATES PATENT AND TRADEMARK OFFICE
CERTIFICATE OF CORRECTION

| | | |
|---|---|---|
| PATENT NO. | : 7,524,940 B2 | Page 1 of 1 |
| APPLICATION NO. | : 10/214037 | |
| DATED | : April 28, 2009 | |
| INVENTOR(S) | : Pelleymounter et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (585) days Delete the phrase "by 585 days" and insert -- by 603 days --

Signed and Sealed this

Fifth Day of January, 2010

David J. Kappos
*Director of the United States Patent and Trademark Office*